United States Patent [19]

Camiener

[11] Patent Number: 5,482,676
[45] Date of Patent: Jan. 9, 1996

[54] VISUALIZATION SYSTEM FOR RETRIEVAL, IDENTIFICATION, AND POSITIONING OF BIOLOGICAL SAMPLES FOR SUBSEQUENT MICROSCOPIC EXAMINATION

[76] Inventor: Gerald W. Camiener, 26700 Hurlingham Rd., Beachwood, Ohio 44122

[21] Appl. No.: 276,593

[22] Filed: Jul. 18, 1994

Related U.S. Application Data

[63] Continuation of Ser. No. 120,337, Sep. 14, 1993, abandoned, which is a continuation of Ser. No. 974,071, Nov. 10, 1992, Pat. No. 5,290,706.

[51] Int. Cl.$^6$ ................................................. A01N 1/02
[52] U.S. Cl. ................................ 422/61; 435/1.1; 435/2; 435/810; 435/40.5; 435/307.1
[58] Field of Search ............................ 422/61; 436/174, 436/176; 435/1, 2, 810

[56] References Cited

U.S. PATENT DOCUMENTS

| | | | |
|---|---|---|---|
| 4,204,978 | 5/1980 | Ibsen et al. | 433/217.1 |
| 4,243,693 | 1/1981 | Nordh | 427/4 |
| 4,447,528 | 5/1984 | Ellis et al. | 435/7.8 |
| 4,640,897 | 2/1987 | Leynadier et al. | 436/501 |
| 4,666,699 | 5/1987 | Slifkin | 424/7.1 |
| 4,731,332 | 3/1988 | Blumenthal et al. | 436/61 |
| 4,828,890 | 5/1989 | Tiedeman et al. | 428/22 |
| 4,894,346 | 1/1990 | Myers et al. | 436/85 |
| 4,946,669 | 8/1990 | Siegfried et al. | 424/4 |
| 4,992,365 | 2/1991 | Hyman | 435/34 |
| 5,026,491 | 6/1991 | Haack et al. | 252/8.552 |
| 5,176,665 | 1/1993 | Watanabe et al. | 604/317 |
| 5,188,935 | 2/1993 | Leif et al. | 435/7.24 |
| 5,190,724 | 3/1993 | Hachmann et al. | 422/28 |
| 5,407,794 | 4/1995 | Kass | 436/63 |

OTHER PUBLICATIONS

*The Merck Index,* 10th Ed., pp. 604–605, 1983.
*Fisher 86* Catalog, 1985, p. 1212.
Benson, H. J., *Microbiological Applications,* 1990, pp. 56–57, 61.

*Primary Examiner*—Robert J. Warden
*Assistant Examiner*—Robert Carpenter
*Attorney, Agent, or Firm*—Foley & Lardner

[57] ABSTRACT

A visualization system for identifying a biological sample in a preservative solution comprising a dye that (i) colors a biological sample in a manner in which the sample can be readily identified and retrieved from among the other contents of the medium; (ii) provides a colored sample that permits proper positioning of the material in a paraffin block prior to sectioning; and (iii) does not interfere with the subsequent processing of the sample at the processing laboratory.

17 Claims, No Drawings

VISUALIZATION SYSTEM FOR RETRIEVAL, IDENTIFICATION, AND POSITIONING OF BIOLOGICAL SAMPLES FOR SUBSEQUENT MICROSCOPIC EXAMINATION

This application is a continuation of U.S. application Ser. No. 08/120,337, filed Sep. 14, 1993, now abandoned; which is a continuation of 07/974,071, filed Nov. 10, 1992, now U.S. Pat. No. 5,290,706.

FIELD OF THE INVENTION

The present invention is directed to a visualization system to be used during the transport of biological samples from the site of collection to the processing laboratory, providing a dye that stains the biological sample so as to make it visible against the background of other components in the medium in the container, and to allow it to be positioned in paraffin so as to provide proper sectioning.

BACKGROUND OF THE INVENTION

Conventionally, a gross biological sample is collected from a mammal and placed in a fixative solution (such as formaldehyde). It is then transported to a laboratory where suitable pieces of the gross sample are retrieved from the solution, sectioned, mounted onto a slide, and finally stained. See e.g., U.S. Pat. Nos. 4,911,915; 5,143,714; 5,137,710; and RE 29,073.

The coloring visualization procedure that is described here is used with biological samples like biopsy tissues, fecal samples containing parasites and discrete organs and tissues like lymph nodes. It is very different from the staining procedures used on sections of tissues as for example those attached to glass slides. In this latter situation, a wide variety of stains may be used to visualize internal cellular structures and components. These latter stains also are used after sectioning.

There also are a group of colorants known under many names including the name "Marker Dyes". These materials are employed to "outline" the outer margins of tissues in a permanent fashion. This group of colorants is distinguished from the subject matter of this invention in at least three important ways.

1. Marker Dyes often are insoluble, permanent, colored materials (or become insoluble and permanent after treatment), and they usually are "painted" onto the tissues.
2. Marker Dyes usually are applied either to fresh tissues, or to tissues after fixation, but before sectioning.
3. The Marker Dye procedure is intended to be permanent so that the margins of the tissues (the painted areas) can be seen easily in the final slide preparation (after sectioning and after staining).

DETAILED DESCRIPTION OF THE INVENTION

The present invention solves two particular problems that occur after transport of biological samples from the site of collection to the processing laboratory. After collection, a sample is usually placed in a fixative solution inside a container and transported to the lab. At the lab, however, it is often difficult to locate and retrieve small biological samples, particularly since they may be transparent and blend in with the background of the fixative solution. The second problem is that, after retrieval, the small sections are often improperly positioned in the paraffin blocks (because they are difficult to see against the white paraffin), and they thereby are not sectioned properly. The present invention solves these two problems by providing a dye that stains the biological sample so as to make it easy to retrieve and easy to position in paraffin blocks, yet which does not interfere with later staining or immunological procedures that are used at the lab to visualize particular components within the sample.

In the broadest sense, the present invention comprises a visualization dye that (i) colors a biological sample in a manner in which said sample can be readily retrieved from among the other contents of said medium; (ii) provides a colored sample that permits proper positioning of the material in a paraffin block prior to sectioning; and (iii) does not interfere with the subsequent processing of said sample at the processing laboratory.

In one embodiment, the present invention is a method of transporting a biological sample from the site of collection from a mammal to a processing laboratory comprising the steps of fixing the biological sample in a fixative agent and staining the biological sample with a visualization dye as described herein.

In another embodiment, the present invention is a composition for transporting a biological sample from the site of collection from a mammal to a processing laboratory comprising a fixative or preservative agents and a dye as defined herein.

Suitable dyes according to the present invention are those that color a biological sample to permit its identification and retrieval from among the contents of a solution without interfering with subsequent examination and other dyes that are applied to the sample at the lab. For example, the dye may be a biological dye or a pH indicator dye. The so called biological dyes appear to act because of their particular affinity for biological tissues and pH indicator dyes appear to work because of their formation of ionic bonds in biological samples. Both permit excellent visualization. Various combinations of these dyes can be used to produce different colors.

Some specific examples of dyes according to the present invention are erythrosine, erioglaucine dye, basic violet 3, tartrazine, amaranth, azocarmine, brilliant blue, bromocresol green, bromothymol blue, carmosine, crystal violet, indigo carmine, pararosaniline, ponceau red, and sunset yellow.

As used herein, the term "biological sample" refers to any biological material, including tissue samples, biopsies, skin shavings, and parasites.

The term "subsequent processing" refers to steps performed after a biological sample is collected and processed, including sectioning, mounting, staining of particular components within the sample, and other immunologic and diagnostic processes performed on the sample in the lab.

The fixative solutions and preservative solutions in which the visualization dyes are used include a variety of water-based fixatives, and alcohol and glycol-based fixative or transport solutions, and combinations thereof, which are known in the art. Also contemplated are preservative solutions as disclosed in U.S. application Ser. No. 07/762,307, now abandoned the entire specification of which is incorporated herein by reference. A preferred preservative solution is HISTOCHOICE™ Tissue Fixatives (products of AMRESCO). The preservative solutions also may contain one or more agents for effecting decalcification while maintaining a biological sample in a pathology-stable form. Other fixative solutions may contain other fixing or preserving agents including glyoxal, formaldehyde, glutaraldehyde, mercuric ions, zinc ions, and picric acid.

As disclosed in U.S. Ser. No. 07/762,307, page 3, the fixative solution comprises an aqueous solution of a $C_{2-6}$ dialdehyde and/or dialdehyde addition product in an amount sufficient to prevent major degenerative changes in said tissue, whereby said tissue remains in a state suitable for macro- or microscopic examination sufficient for pathological or experimental examination.

As disclosed on page 5 of U.S. Ser. No. 07/762,307, the fixative solutions preferably contain an ionic or nonionic chemical in an amount of from about 0.1% to about 14% of said solution, whereby the osmotic pressure effects of said solution is altered, thereby modifying and/or stabilizing said tissue for subsequent examination. In one such embodiment, sea lamprey eels are stabilized using a dialdehyde solution containing 3% sodium chloride.

In a further embodiment, the fixative solution may preferably kill and/or inhibit microorganisms that otherwise might be present or develop and thereby degrade the specimen, as disclosed in U.S. Ser. No. 07/762,307, page 10, lines 22–25.

The concentration of visualization dye is adjusted according to the particular dye which is selected, according to its color intensity, and according to the desired level of coloring of the biological sample. The general range of dye concentration is from 0.5 to 1,000 ppm of fixative solution.

As disclosed in U.S. Ser. No. 07/762,307, page 4, lines 13–21, the aqueous fixative solutions may also include from about 0.15% to about 36% of a $C_{1-4}$ alkane-mono, di-, or triol. Alkanols include monools like ethanol, diols like ethylene glycol, and triols like glycerol. Glycerol is particularly suited for a stabilizing solution that has as one of its objectives the maintenance of a tissue sample in a more pliable condition. Mono-and diol-alkanes are particularly useful in permitting faster tissue penetration of the stabilizing solution which is very important for preserving larger tissue samples and organs.

The present invention is more clearly illustrated by, though in no way limited to, the following examples:

EXAMPLES

Example 1

Erythrosine dye was added to HISTOCHOICE™ Tissue Preservative (water-based) at a concentration of 10 ppm, and biopsy samples from a skin lesion were placed in the solution (10–20 times volume excess of the solution). The skin samples could be seen easily in the solution after just 10 minutes, and the samples became much redder in color over the next two days. The samples were easily retrieved from the solution and visualized for positioning in the paraffin block. No red color was visible after sectioning. The microscopic detailed appearance of the tissue was excellent, and it was equivalent to control tissue preserved and treated in the same way except that the dye was absent.

Example 2

The experiment described in Example 1 was repeated using OMNIFIX™ Tissue Preservative (water, alcohol, and glycol-based) in place of HISTOCHOICE™. The results were about the same as those in Example 1, except that the microscopic detail was not as good with the OMNIFIX™. The visualization effects of the dye, however, were equal to Example 1.

Example 3

The experiment described in Example 1 was repeated except that the tissue was visualized using an immunohistochemical reagent for keratin instead of the usual hematoxylin and eosin stains. The microscopic detailed appearance of the tissue was excellent, and there was no reduction in the amount of keratin-based staining as compared to controls prepared in exactly the same way except without the visualization dye.

Example 4

Erioglaucine dye was added to HISTOCHOICE™ Tissue Preservative (water-based) at a concentration of 100 ppm, and fecal samples containing tape worm segments and ova were added to the solution (5 times volume excess of preservative solution). After two days, the fecal contamination material was separated from the parasite segments and ova by differential centrifugation. The parasite segments and ova were easily visible and easily retrieved for microscopic examination. The presence of the dye in the solution increased the speed of the identification process.

Example 5

Basic violet 3 was added to HISTOCHOICE™ Tissue Preservative (water-based, containing 0.5 N HCl) at a concentration of 300 ppm, and 0.5 cm square pieces of cortical bone were added to the solution (50 times volume excess of preservative solution). The bone samples could be easily seen in the solution after just 10 minutes, and the color of the bone pieces intensified considerably over the next 18 hours. The bone samples were easily retrieved from the decalcifying solution and easily visualized during positioning in the paraffin block. No color was seen after sectioning. The microscopic detailed appearance of the tissue was excellent and equivalent to control tissue treated in the same way except without the visualization dye.

Example 6

A mixture of dyes (tartrazine dye, 4.5 ppm and erioglaucine dye, 2 ppm) was prepared in HISTOCHOICE™ at the indicated final concentrations. Several pieces of bloody uterine tissue obtained by curettage during a "D & C" procedure were added to the solution (10 times volume excess of preservative solution). The samples were easily seen and retrieved from the solution after 5 hours, and the samples were visualized easily after sectioning. The microscopic detailed appearance of the tissue was excellent and equivalent to control tissues preserved and treated the same way, except without the dye mixture.

Example 7

The experiment described in Example 6 was repeated using 10% neutral buffered formalin in place of HISTOCHOICE™. The results were about the same as those in Example 6, except that the microscopic detail was not as good with the formalin. The visualization effects of the dye, however, were equal to Example 6.

Example 8

The experiment described in Example 6 was repeated using B5 fixative containing mercury ion in place of HISTOCHOICE™, and lymph node tissue in place of uterine tissue. The results were about the same as those in Example 6, including the visualization effects of the dye.

I claim:

1. A kit for maintaining and/or transporting a biological sample which consists of a male receptacle means, a female closure means, a fixative medium, and a visualization-effective amount of a dye that (i) colors said sample in a manner in which said sample can be readily identified from among the other contents of said medium; and (ii) does not interfere with the subsequent processing of said sample at the processing laboratory;

wherein said fixative medium and said dye are contained in the male receptacle means, and the fixative medium consists essentially of a fixative-effective amount of an aqueous solution of formaldehyde or a $C_{2-6}$ dialdehyde except for glutaraldehyde or a mixture thereof.

2. A kit according to claim 1, wherein the dye is selected from the group consisting of erythrosine, erioglaucine, basic violet 3, tartrazine, amaranth, azocarmine, brilliant blue, bromocresol green, bromothymol blue, carmosine, crystal violet, indigo carmine, pararosaniline, ponceau red, sunset yellow and combinations thereof.

3. A kit according to claim 2, wherein the fixative medium is osmotically controlled with an ionic or nonionic chemical.

4. A kit according to claim 1, wherein the fixative medium consists essentially of an aqueous solution of formaldehyde or glyoxal.

5. A kit according to claim 4, wherein the fixative medium is osmotically controlled with an ionic or nonionic chemical.

6. A kit for maintaining and/or transporting a biological sample which consists of a male receptacle means, a female closure means, a fixative medium, and a visualization-effective amount of a dye that (i) colors said sample in a manner in which said sample can be readily identified from among the other contents of said medium; and (ii) does not interfere with the subsequent processing of said sample at the processing laboratory;

wherein said fixative medium and said dye are contained in the male receptacle means, and the fixative medium consists essentially of a fixative-effective amount of an aqueous solution of an antimicrobial agent except for alkane mono-, di-, or triol alcohols and glycols.

7. A kit according to claim 6, wherein the dye is selected from the group consisting of erythrosine, erioglaucine, basic violet 3, tartrazine, amaranth, azocarmine, brilliant blue, bromocresol green, bromothymol blue, carnosine, crystal violet, indigo carmine, pararosaniline, ponceau red, sunset yellow and combinations thereof.

8. A kit according to claim 6, wherein the fixative medium is osmotically controlled with an ionic or nonionic chemical.

9. A kit according to claim 6, wherein the fixative medium further contains an aldehyde.

10. A kit for maintaining and/or transporting a biological sample which consists of a mule receptacle means, a female closure means, a fixative medium, and a visualization-effective amount of a dye that (i) colors said sample in a manner in which said sample can be readily identified from among the other contents of said medium; and (ii) does not interfere with the subsequent processing of said sample at the processing laboratory;

wherein said fixative medium and said dye are contained in the male receptacle means, and the fixative medium consists essentially of (i) a fixative-effective amount of an aqueous solution of formaldehyde or a $C_{2-6}$ dialdehyde except for glutaraldehyde or a mixture thereof and (ii) a non-fixative amount of an alcohol or a combination of alcohols selected from the group consisting of alkane mono-, di-, or triol alcohols and glycols for promoting penetration of the fixative medium into the biological sample, said non-fixative amount of alcohol being in the range of about 0.15% to about 36%.

11. A kit according to claim 10, wherein the fixative medium consists essentially of an aqueous solution of formaldehyde or glyoxal.

12. A kit according to claim 11, wherein the fixative medium is osmotically controlled with an ionic or nonionic chemical.

13. A kit according to claim 10, wherein the dye is selected from the group consisting of erythrosine, erioglaucine, basic violet 3, tartrazine, amaranth, azocarmine, brilliant blue, bromocresol green, bromothymol blue, carmosine, crystal violet, indigo carmine, pararosaniline, ponceau red, sunset yellow and combinations thereof.

14. A kit according to claim 10, wherein the fixative medium is osmotically controlled with an ionic or nonionic chemical.

15. A kit for maintaining and/or transporting a biological sample which consists of a male receptacle means, a female closure means, a fixative medium, and a visualization-effective amount of a dye that (i) colors said sample in a manner in which said sample can be readily identified from among the other contents of said medium; and (ii) does not interfere with the subsequent processing of said sample at the processing laboratory;

wherein said fixative medium and said dye are contained in the male receptacle means, and the fixative medium consists essentially of (i) a fixative-effective amount of an aqueous solution of an antimicrobial agent and (ii) a non-fixative amount of an alcohol or a combination of alcohols selected from the group consisting of alkane mono-, di-, or triol alcohols and glycols for promoting penetration of the fixative medium into the biological sample, said non-fixative amount of alcohol being in the range of about 0.15% to about 36%.

16. A kit according to claim 15, wherein the dye is selected from the group consisting of erythrosine, erioglaucine, basic violet 3, tartrazine, amaranth, azocarmine, brilliant blue, bromocresol green, bromothymol blue, carmosine, crystal violet, indigo carmine, pararosaniline, ponceau red, sunset yellow and combinations thereof.

17. A kit according to claim 15, wherein the fixative medium is osmotically controlled with an ionic or nonionic chemical.

* * * * *